(12) United States Patent
Biedermann et al.

(10) Patent No.: US 9,289,246 B2
(45) Date of Patent: *Mar. 22, 2016

(54) BONE ANCHORING DEVICE (71) Applicant: Biedermann Technologies GmbH & Co. KG, Donaueschingen (DE)

(72) Inventors: Lutz Biedermann, VS-Villingen (DE); Wilfried Matthis, Weisweil (DE); Berthold Dannecker, St. Georgen (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/584,287

(22) Filed: Dec. 29, 2014

(65) Prior Publication Data
US 2015/0209085 A1    Jul. 30, 2015

Related U.S. Application Data (63) Continuation of application No. 13/466,773, filed on May 8, 2012, now Pat. No. 8,940,024, which is a continuation of application No. 12/183,932, filed on Jul. 31, 2008, now Pat. No. 8,192,470.

(60) Provisional application No. 60/953,170, filed on Jul. 31, 2007.

(30) Foreign Application Priority Data

Jul. 31, 2007   (EP) .................................... 07015041

(51) Int. Cl.
*A61B 17/70*    (2006.01)
(52) U.S. Cl.
CPC ......... *A61B 17/7037* (2013.01); *A61B 17/7034* (2013.01); *A61B 17/7032* (2013.01)

(58) Field of Classification Search
CPC ..................... A61B 17/7032; A61B 17/7037
See application file for complete search history.

(56) References Cited

U.S. PATENT DOCUMENTS

| 4,946,458 | A | 8/1990 | Harms et al. |
| 5,443,467 | A | 8/1995 | Biedermann et al. |

(Continued)

FOREIGN PATENT DOCUMENTS

| CN | 1359660 A | 7/2002 |
| DE | 43 05 576 A1 | 8/1994 |

(Continued)

OTHER PUBLICATIONS

Extended European Search Report for European Application No. 08022510.5, European Search Report dated Apr. 16, 2009 and mailed Apr. 27, 2009 (7 pgs.).

(Continued)

*Primary Examiner* — Andrew Yang
(74) *Attorney, Agent, or Firm* — Lewis Roca Rothgerber Christie LLP (57) ABSTRACT

A bone anchoring device includes a bone anchoring element having a shaft for anchoring in the bone and a head; and a receiving part for coupling a rod to the bone anchoring element. The receiving part includes a first portion with a first end and a second end and a U-shaped recess for receiving the rod, the recess extending from the first end in the direction of the second end thereby forming two free legs and a second portion at the side of the second end opposite to the first end for accommodating the head, the second portion having a free end and being flexible so as to allow introduction and clamping of the head. The bone anchoring device also includes a locking ring embracing the second portion. The head is locked by means of exerting pressure with the rod onto the locking ring resulting in compression of the second portion of the receiving part and wherein the locking ring is mounted to the receiving part from the free end of the second portion.

20 Claims, 10 Drawing Sheets (56) References Cited

U.S. PATENT DOCUMENTS

| | | |
|---|---|---|
| 5,549,608 A | 8/1996 | Errico et al. |
| 5,575,792 A | 11/1996 | Errico et al. |
| 5,578,033 A | 11/1996 | Errico et al. |
| 5,584,834 A | 12/1996 | Errico et al. |
| 5,586,984 A | 12/1996 | Errico et al. |
| 5,609,593 A | 3/1997 | Errico et al. |
| 5,672,176 A | 9/1997 | Biedermann et al. |
| 5,688,273 A | 11/1997 | Errico et al. |
| 5,728,098 A | 3/1998 | Sherman et al. |
| 5,733,285 A | 3/1998 | Errico et al. |
| 5,782,831 A | 7/1998 | Sherman et al. |
| 5,899,904 A | 5/1999 | Errico et al. |
| 5,964,760 A | 10/1999 | Richelsoph |
| 6,010,503 A | 1/2000 | Richelsoph et al. |
| 6,050,997 A | 4/2000 | Mullane |
| 6,063,090 A | 5/2000 | Schläpfer |
| 6,132,432 A | 10/2000 | Richelsoph |
| 6,251,111 B1 | 6/2001 | Barker et al. |
| 6,254,602 B1 | 7/2001 | Justis |
| 6,273,888 B1 | 8/2001 | Justis |
| 6,355,040 B1 | 3/2002 | Richelsoph et al. |
| 6,368,321 B1 | 4/2002 | Jackson |
| 6,371,957 B1 | 4/2002 | Amrein et al. |
| 6,454,773 B1 | 9/2002 | Sherman et al. |
| 6,471,705 B1 | 10/2002 | Biedermann et al. |
| 6,582,436 B2 | 6/2003 | Schlapfer et al. |
| 6,623,485 B2 | 9/2003 | Doubler et al. |
| 6,964,665 B2 | 11/2005 | Thomas et al. |
| 7,073,415 B2 | 7/2006 | Casutt et al. |
| 7,090,674 B2 | 8/2006 | Doubler et al. |
| 7,105,029 B2 | 9/2006 | Doubler et al. |
| 7,291,151 B2 | 11/2007 | Alvarez |
| 7,322,981 B2 | 1/2008 | Jackson |
| 7,335,201 B2 | 2/2008 | Doubler et al. |
| 7,468,064 B2 | 12/2008 | Bruneau et al. |
| 7,585,315 B2 | 9/2009 | Donath |
| 7,591,836 B2 | 9/2009 | Dick et al. |
| 7,604,655 B2 | 10/2009 | Warnick |
| 7,604,656 B2 | 10/2009 | Shluzas |
| 7,674,277 B2 | 3/2010 | Burd et al. |
| 7,678,136 B2 | 3/2010 | Doubler et al. |
| 7,682,377 B2 | 3/2010 | Konieczynski et al. |
| 7,833,251 B1 | 11/2010 | Ahlgren et al. |
| 7,942,906 B2 | 5/2011 | Bishop |
| 7,981,143 B2 | 7/2011 | Doubler et al. |
| 7,988,694 B2 | 8/2011 | Barrus et al. |
| 8,192,470 B2 | 6/2012 | Biedermann et al. |
| 8,328,817 B2 | 12/2012 | Strauss |
| 8,506,609 B2 | 8/2013 | Biedermann et al. |
| 8,506,610 B2 | 8/2013 | Biedermann et al. |
| 8,636,782 B2 | 1/2014 | Biedermann et al. |
| 2001/0005796 A1 | 6/2001 | Zdeblick et al. |
| 2001/0047173 A1 | 11/2001 | Schlapfer et al. |
| 2002/0032443 A1 | 3/2002 | Sherman et al. |
| 2002/0082602 A1 | 6/2002 | Biedermann et al. |
| 2003/0023240 A1 | 1/2003 | Amrein et al. |
| 2005/0080415 A1 | 4/2005 | Keyer et al. |
| 2005/0080420 A1 | 4/2005 | Farris et al. |
| 2005/0096653 A1 | 5/2005 | Doubler et al. |
| 2005/0137594 A1 | 6/2005 | Doubler et al. |
| 2005/0228385 A1 | 10/2005 | Iott et al. |
| 2005/0228392 A1 | 10/2005 | Keyer et al. |
| 2006/0025769 A1 | 2/2006 | Dick et al. |
| 2006/0089644 A1 | 4/2006 | Felix |
| 2006/0161153 A1 | 7/2006 | Hawkes et al. |
| 2006/0173456 A1 | 8/2006 | Hawkes et al. |
| 2006/0200128 A1 | 9/2006 | Mueller |
| 2006/0243616 A1 | 11/2006 | Caron |
| 2007/0093817 A1 | 4/2007 | Barrus et al. |
| 2007/0093818 A1 | 4/2007 | Biedermann et al. |
| 2007/0119871 A1 | 5/2007 | Garcia |
| 2007/0123862 A1 | 5/2007 | Warnick |
| 2007/0161999 A1 | 7/2007 | Biedermann et al. |
| 2007/0213722 A1 | 9/2007 | Jones et al. |
| 2007/0270813 A1 | 11/2007 | Garamszegi |
| 2007/0270839 A1 | 11/2007 | Jeon et al. |
| 2007/0270842 A1 | 11/2007 | Bankoski et al. |
| 2007/0276379 A1 | 11/2007 | Miller et al. |
| 2007/0288004 A1 | 12/2007 | Alvarez |
| 2008/0009862 A1 | 1/2008 | Hoffman |
| 2008/0009863 A1 | 1/2008 | Bond et al. |
| 2008/0015576 A1 | 1/2008 | Whipple |
| 2008/0027432 A1 | 1/2008 | Strauss et al. |
| 2008/0045950 A1 | 2/2008 | Dewey |
| 2008/0108992 A1 | 5/2008 | Barry et al. |
| 2008/0119857 A1 | 5/2008 | Potash et al. |
| 2008/0147129 A1 | 6/2008 | Biedermann et al. |
| 2008/0154315 A1 | 6/2008 | Jackson |
| 2008/0161859 A1 | 7/2008 | Nilsson |
| 2008/0183215 A1 | 7/2008 | Altarac et al. |
| 2008/0183216 A1 | 7/2008 | Jackson |
| 2008/0234750 A1 | 9/2008 | Woods et al. |
| 2008/0234761 A1 | 9/2008 | Jackson |
| 2008/0243193 A1 | 10/2008 | Ensign et al. |
| 2008/0249576 A1 | 10/2008 | Hawkes et al. |
| 2008/0269809 A1 | 10/2008 | Garamszegi |
| 2008/0294202 A1 | 11/2008 | Peterson et al. |
| 2008/0294203 A1 | 11/2008 | Kovach et al. |
| 2009/0012567 A1 | 1/2009 | Biedermann et al. |
| 2009/0018591 A1 | 1/2009 | Hawkes et al. |
| 2009/0036934 A1 | 2/2009 | Biedermann et al. |
| 2009/0062865 A1 | 3/2009 | Schumacher |
| 2009/0062867 A1 | 3/2009 | Schumacher |
| 2009/0105716 A1 | 4/2009 | Barrus |
| 2009/0105756 A1 | 4/2009 | Richelsoph |
| 2009/0105769 A1 | 4/2009 | Rock et al. |
| 2009/0105770 A1 | 4/2009 | Berrevoets et al. |
| 2009/0143827 A1 | 6/2009 | Levy et al. |
| 2009/0149887 A1 | 6/2009 | Schlaepfer et al. |
| 2009/0157125 A1 | 6/2009 | Hoffman et al. |
| 2009/0228054 A1 | 9/2009 | Hoffman et al. |
| 2009/0266728 A1 | 10/2009 | Turner et al. |
| 2010/0063545 A1 | 3/2010 | Richelsoph |
| 2010/0076490 A1 | 3/2010 | Greenwald et al. |
| 2010/0114180 A1 | 5/2010 | Rock et al. |
| 2010/0137875 A1 | 6/2010 | Marino et al. |
| 2010/0137915 A1 | 6/2010 | Anderson et al. |
| 2010/0160975 A1 | 6/2010 | Biedermann et al. |
| 2010/0160976 A1 | 6/2010 | Biedermann et al. |
| 2010/0168800 A1 | 7/2010 | Biedermann et al. |
| 2010/0168801 A1 | 7/2010 | Biedermann et al. |
| 2010/0198272 A1 | 8/2010 | Keyer et al. |
| 2011/0276098 A1 | 11/2011 | Biedermann et al. |
| 2012/0124813 A1 | 5/2012 | Biedermann et al. |
| 2012/0165874 A1 | 6/2012 | Biedermann et al. |
| 2012/0172932 A1 | 7/2012 | Biedermann et al. |
| 2012/0179209 A1 | 7/2012 | Biedermann et al. |
| 2012/0179211 A1 | 7/2012 | Biedermann et al. |
| 2012/0283789 A1 | 11/2012 | Biedermann et al. |

FOREIGN PATENT DOCUMENTS

| | | |
|---|---|---|
| EP | 0 242 708 A2 | 4/1987 |
| EP | 0 836 835 A2 | 4/1998 |
| EP | 0 947 174 A2 | 10/1999 |
| EP | 0 951 245 B1 | 10/1999 |
| EP | 1 749 489 A1 | 2/2007 |
| EP | 1 923 011 A1 | 5/2008 |
| EP | 2 022 423 A1 | 2/2009 |
| EP | 2 191 780 A1 | 6/2010 |
| FR | 2 854 143 A1 | 10/2004 |
| JP | 8-257035 | 10/1996 |
| JP | 10-225467 A | 8/1998 |
| JP | 11-318933 | 11/1999 |
| JP | 2001-505469 A | 4/2001 |
| JP | 2007-38009 | 2/2007 |
| JP | 2007-510468 | 4/2007 |
| JP | 2007-516811 | 6/2007 |
| JP | 2008-541880 A | 11/2008 |
| WO | WO 98/32386 A1 | 7/1998 |
| WO | WO 00/18310 A1 | 4/2000 |
| WO | WO 00/72769 A1 | 12/2000 |
| WO | WO 00/72770 A1 | 12/2000 |
| WO | WO 2004/089245 A2 | 10/2004 |

(56) References Cited

FOREIGN PATENT DOCUMENTS

| WO | WO 2005/041821 A2 | 5/2005 |
|---|---|---|
| WO | WO 2005/065413 A2 | 7/2005 |
| WO | WO 2006/116437 A2 | 11/2006 |
| WO | WO 2006/127992 A2 | 11/2006 |
| WO | WO 2007/011431 A2 | 1/2007 |
| WO | WO 2007/038350 A2 | 4/2007 |
| WO | WO 2007/038351 A3 | 4/2007 |
| WO | WO 2007/047711 A2 | 4/2007 |
| WO | WO 2007/075454 A1 | 7/2007 |
| WO | WO 2007/117366 A2 | 10/2007 |

OTHER PUBLICATIONS

Extended European Search Report for European Application No. 08022553.5, European Search Report dated May 18, 2009 and mailed May 28, 2009 (7 pgs.).

Extended European Search Report for European Application No. 09002468.8, European Search Report dated May 5, 2009 and mailed May 18, 2009 (7 pgs.).

Extended European Search Report for European Application No. 10162063.1, European Search Report dated Jul. 14, 2010 and mailed Jul. 22, 2010 (5 pgs.).

Extended European Search Report for European Application No. 10162063.1, European Search Report dated Oct. 5, 2010 and mailed Oct. 13, 2010 (10 pgs.).

Extended European Search Report for European Application No. 10192278.9, European Search Report dated Feb. 16, 2011 and mailed Feb. 23, 2011 (7 pgs.).

Office action for U.S. Appl. No. 12/645,3358, dated May 21, 2012, 8 sheets.

Office action for U.S. Appl. No. 12/645,335, dated Oct. 31, 2012, 9 sheets.

Office action for U.S. Appl. No. 12/649,194, dated May 23, 2012, 7 sheets.

Office action for U.S. Appl. No. 12/649,236, dated May 18, 2012, 11 sheets.

Final Office action for U.S. Appl. No. 12/649,236, dated Dec. 20, 2012, 11 sheets.

Office action for U.S. Appl. No. 12/709,375, dated Dec. 5, 2011, 7 sheets.

Final Office action for U.S. Appl. No. 12/709,375, dated Jul. 10, 2012, 6 sheets.

Office action for U.S. Appl. No. 12/709,375, dated Sep. 13, 2013, 6 sheets.

Final Office action for U.S. Appl. No. 12/709,375, dated Jun. 4, 2014, 5 sheets.

Office action for U.S. Appl. No. 13/101,989, dated Jan. 31, 2013, 22 sheets.

European Search Report dated Feb. 20, 2008 for EPO Application No. EP 07015041.2, European Search Report mailed Mar. 3, 2008, Biedermann Motech GmbH (8 pp.).

BONE ANCHORING DEVICE

RELATED APPLICATION(S)

This application is a continuation of U.S. patent application Ser. No. 13/466,773, filed May 8, 2012, which is a continuation of U.S. patent application Ser. No. 12/183,932, filed Jul. 31, 2008, now U.S. Pat. No. 8,192,470, which claims the benefit of U.S. Provisional Patent Application Ser. No. 60/953,170, filed Jul. 31, 2007, the contents of which are hereby incorporated by reference in their entirety, and claims priority from European Patent Application EP 07 015 041.2, filed Jul. 31, 2007, the contents of which are hereby incorporated by reference in their entirety.

BACKGROUND

The present application relates to a bone anchoring device.

Various designs of polyaxial bone screws are known wherein each design has particular characteristics and wherein different locking principles are used.

DE 43 05 576 C1 describes a polyaxial bone screw having a screw element and a receiving part and a pressure element acting onto the head of the screw element to press it down against the seat in the receiving part in order to lock the rotational position of the head. The bone screw usually is preassembled so that the screw element is screwed into the bone with the receiving part mounted on the screw element.

Other bone screws are known wherein the head is clamped from the side to lock the rotational position. EP 0 242 708 A2 describes a bone screw with a receiving part consisting of two spherically-shaped halves pressing from two lateral sides onto the spherical head. The halves are held together in their lower portion by a ring.

U.S. Pat. No. 5,672,176 discloses a bone screw with a receiving part with a conically shaped seat and a conically-shaped pressure element which exerts pressure onto the head from above and from the side. If the cone angle has a value lying within a specific range self-locking of the pressure element within the receiving part takes place which allows to preliminary lock the head within the receiving part while the rod is still moveable in order to allow the adjustment of its position.

EP 0 951 245 B1 describes a bone screw with a receiving part having a conically-shaped cavity accommodating the head wherein a spring chuck is provided in the cavity which is downwardly and radially compressible to clamp the head. With this bone screw it is possible to click the receiving part onto the head of the screw element which allows to screw the screw element into the bone and to connect it to the receiving part thereafter.

U.S. Pat. No. 5,728,098 discloses a bone screw for connection to a spinal rod comprising a screw element and a receiver member which has slits provided at the bottom of the rod receiving channel and wherein two locking rings made of a shape memory alloy are provided one at the lower side of the receiver member and one of the upper side. The locking rings contract about the portions of the receiver member when the temperature is elevated so that the rod is clamped in the channel.

U.S. Pat. No. 5,549,608 discloses a polyaxial bone screw with a screw element with a spherical head and a coupling element to couple the screw element to a spinal rod. The coupling element has a tapered lower portion including a slotted interior chamber in which the spherical head is initially polyaxially disposed. The coupling element further has a recess for receiving the head. In addition, a locking ring surrounding the lower portion of the coupling element and a cylindrical rod securing sleeve which fits over the coupling element are provided. A locking nut is used to exert pressure onto the rod securing sleeve. The head is locked in the interior chamber by means of the locking ring which is pressed down by the rod securing sleeve. U.S. Pat. No. 5,575,792 discloses a similar device using a hook instead of a bone screw. In contrast to the afore-mentioned bone screw the rod securing sleeve is omitted and the rod directly presses onto the locking ring. The locking ring has to be placed onto the coupling element from above. It is not secured against escaping towards the upper end and against rotation when the rod is not inserted. Furthermore, the size of this known bone anchoring device is quite large as the locking ring and the locking nut extend substantially outward from the diameter of the coupling element.

Based on the foregoing, there is a need to provide an improved bone anchoring device which comprises a minimum number of parts and which has a small size while simultaneously providing a safe locking and can be used as a modular system.

SUMMARY

A bone anchoring device according to aspects of the disclosure includes a bone anchoring element and a receiving part for connection to a rod. The head of the bone anchoring element is locked in the receiving part by compression of a portion of the receiving part laterally surrounding the head by means of a locking ring which is pressed down by the rod. The portion of the receiving part which clamps the head is designed so as to allow the locking ring to be mounted from the free end of the portion. The bone anchoring device can be realized, for example, in form of a polyaxial bone screw allowing a pivotal movement of the head or in form of a monoaxial bone screw allowing a rotational movement of the head around a single axis in the unlocked state, respectively.

The bone anchoring device according to the aspects of the disclosure includes only few elements which reduces the costs of manufacturing and facilitates handling. It makes use of the principle of clamping the head of the bone anchoring element circumferentially from the lateral sides which reduces the force necessary to safely clamp the head. The design of the bone anchoring device allows to further reduce the dimension in terms of height as well as in terms of the diameter which makes it particularly suitable for applications where small-sized anchoring devices are required such as in the field of cervical spine surgery or pediatric applications, trauma and minimal open applications for bone surgery.

The receiving part can be clicked onto the head of the bone anchoring element at any time before and during surgery. Therefore, it is for example possible to first anchor the bone anchoring element in the bone and thereafter connect it to the receiving part and the rod.

By selecting an appropriate angle of the conically-shaped lower portion of the receiving part and the locking ring, it is possible to achieve a self-locking of the head in the lower portion. Alternatively, this can be achieved by roughening the connecting surfaces of the locking ring and the receiving part. This allows secondary adjustments of the rod without loosening the fixation of the head.

Further features and advantages of the invention will become apparent from the description of embodiments using the accompanying drawings.

DETAILED DESCRIPTION OF THE INVENTION

As shown in FIGS. 1 to 5, the bone anchoring device according to a first embodiment includes a bone anchoring element 1 in the form of a bone screw having a threaded shaft 2 and a spherical segment-shaped head 3. The head 3 has a recess 4 for engagement with a screwing-in tool. The bone anchoring device further comprises a receiving part 5 for receiving a rod 6 to connect it to the bone anchoring element 1. Further, a closure element 7 in form of an inner screw or set screw is provided for securing the rod 6 in the receiving part 5. In addition, the bone anchoring device comprises a locking ring 8 for locking the head in the receiving part 5.

As can be seen in particular in FIGS. 6 to 10, the receiving part 5 comprises a first portion 9 which is substantially cylindrical and which has first end 9a and an opposite second end 9b. The first portion 9 has a coaxial first bore 10 provided at the second end 9b. The diameter of the first bore 10 is smaller than the diameter of the head 3 of the bone anchoring element. The first portion 9 also comprises a coaxial second bore 11 extending from the first end 9a to a distance from the second end 9b. The diameter of the second bore 11 is larger than that of the first bore 10 and larger than the diameter of the rod 6. A U-shaped recess 12 is provided in the first portion which extends from the first end 9a to the second end 9b the diameter of the U-shaped recess being slightly larger than the diameter of the rod 6 in such a way that the rod 6 can be placed in the recess and is guided therein. By means of the U-shaped recess 12 two free legs 12a, 12b are formed on which an internal thread 13 is provided. The internal thread can be a metric thread, a flat thread, a negative angle thread, a saw-tooth thread or any other thread. Preferably, a thread form such as a flat thread or a negative angle thread is used which prevents splaying of the legs 12a, 12b when the inner screw 7 is screwed-in. The depth of the U-shaped recess is such that the rod 6 and the inner screw 7 can be inserted between the legs. Between the bottom of the recess 12 and the legs 12a, 12b a flat section 14 is provide forming the end of the bore 11.

The first portion 9 of the receiving part 5 further comprises a plurality of coaxial slits 15 extending from the second end 9b to a distance from the first end wherein the distance corresponds approximately to the length of the internal thread 13. The slits 15 are open at the second end 9b and extend, as can be seen in particular in FIGS. 6, 9 and 10 through the flat section 14 and the U-shaped recess 12. At least one slit 15, and preferably more than one slit is provided on either side of the U-shaped recess. The number of slits is selected according to the degree of elasticity which shall be provided by the slits. The number of slits may depend on the material and the wall thickness and/or other factors.

Adjacent to the second end 9b the receiving part 5 includes a second portion 16 providing an accommodation space for the head 3 of the bone anchoring element 1. The second portion 16 has a conically-shaped outer surface including a cone angle α which tapers towards the second end 9b and which has a free end 17 opposite to the second end 9b. As can be seen in particular in FIG. 4, the outer diameter of the first portion 9 at its second end 9b is larger than the outer diameter of the second portion 16 adjacent to the second end 9b and also larger than the outer diameter of the second portion at its free end 17. Hence, the second portion 16 is recessed with respect to the first portion 9. The second portion 16 has an internal hollow spherical section 18 forming a seat for the spherical segment-shaped head 3 of the bone anchoring element 1. The hollow spherical section 18 is dimensioned in such a way that it encompasses the head 3 of the bone anchoring element from the side covering a region including the largest diameter of the head 3. As can be seen in FIGS. 1, 6, 9 and 10 cuts 24 are provided in the first portion on either end of the channel formed by the recess 12.

As can be seen in particular in FIGS. 6 to 10, a plurality of slits 19 are provided which are open to the free end 17 and extend from the free end 17 to the second end 9b of the first portion and continue in the slits 15 of the first portion thereby forming a continuous slit extending from the free end 17 of the second portion into the first portion. The number of slits 19 may be equal to the number of the slits 15, however, it can be smaller or larger depending on the desired elasticity of the second portion 16. In addition, slits 20 are provided on the side of the second portion 16 which is adjacent to the U-shaped recess 12 of the first portion. The slits 20 end at a distance from the second end 9b. The elasticity of the second portion 16 is such that the head 3 of the anchoring element can be inserted by expanding the second portion and can be clamped by compressing the second portion. The slits 15 in the first portion facilitate mounting of the receiving part onto the head 3 manually, for example at any time before or during surgery. The dimension of the head 3 and the elasticity of the second portion is designed such that when the head is introduced into the second portion it is temporarily held in a preliminary angular holding position due to frictional forces. This preliminary holding position can be selected by rotating the receiving part against the head. It prevents an uncontrolled movement of the receiving part once the bone screw is implanted and the receiving part is put onto the head.

Figure 4:
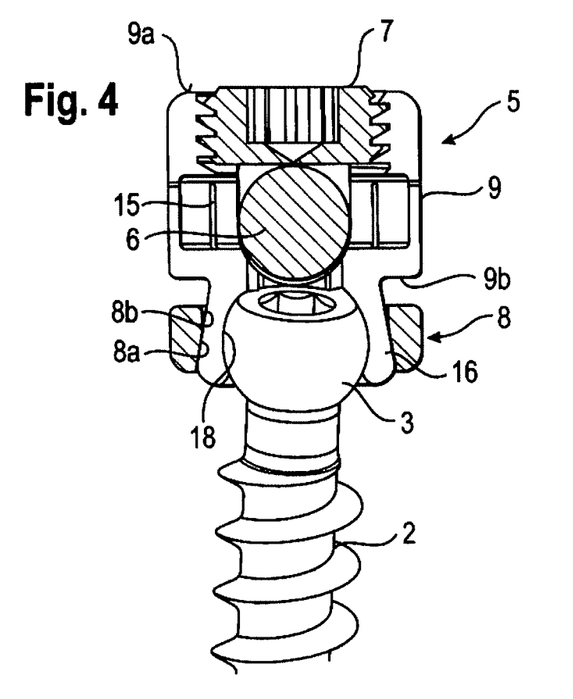
FIG. 4 shows a partial sectional view of the bone anchoring device of FIGS. 1 to 3 in a section perpendicular to the rod axis.

The locking ring 8 will now be described with reference to FIGS. 1, 4 and 5. The locking ring 8 has a substantially cylindrical outer surface with an outer diameter corresponding to the outer diameter of the first portion 9 of the receiving part 5. The height of the locking ring 8 in an axial direction is smaller than that of the second portion 16 of the receiving part 5 so that, as shown in FIG. 4, there is a distance between the locking ring 8 and the second end 9b of the receiving part 5 when the locking ring 8 is in its position clamping the head 3.

The elasticity of the second portion 16 and the size of the second portion at the free end 17 allows to mount the locking ring by clicking it from the free end 17 onto the second portion 16. Since the outer diameter of the second portion is smaller than that of the first portion 9, the locking ring does not project beyond the first portion in a radial direction.

The locking ring 8 has on its inner side a first section 8a and adjacent thereto a second section 8b. The first section 8a is conically-shaped corresponding to the conical outer wall of the second portion 16 of the receiving part 5. The first section 8b is cylindrical. As can be seen in particular in FIG. 4, the dimensions of the first section 8a and the second section 8b of the locking ring are such that the locking ring 8 can slide along the outer surface of the second portion 16 and thereby compressing the second portion 16 increasingly when sliding downward. If the rod is not yet inserted or not pressed into the recess 12, the locking ring is movable between a first position limited by the second end 9b which acts as a stop and the free end 17 of the second portion which prevents escaping due to the conical shape.

If the cone angle α is selected to be between approximately 2° and 10°, a self-locking can be achieved between the locking ring and the second portion which means that an additional force would be required to loosen the locking ring once it has clamped the head 3. If the cone angle α is larger than approximately 10°, no self-locking effect is present. Of course, the angles at which a self-locking effect can be achieved depend on the materials used and the treatment of the surfaces engaging each other.

Figure 1:
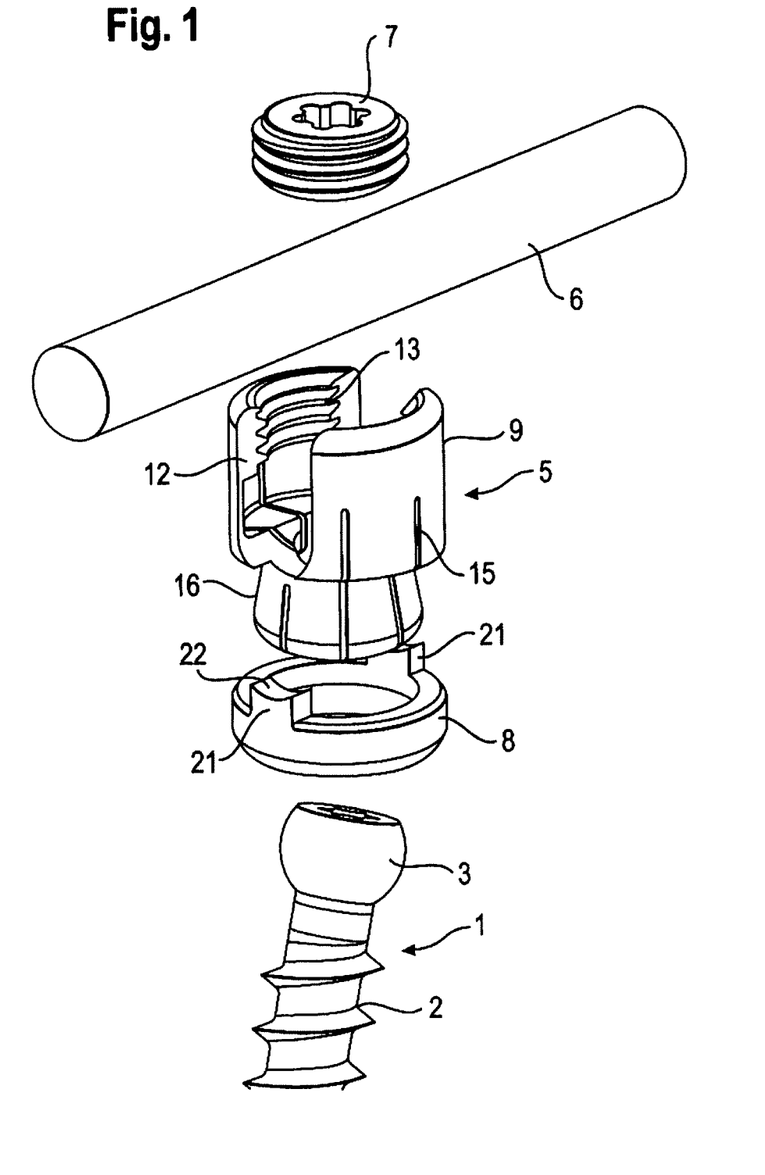
FIG. 1 shows a perspective exploded view of a first embodiment of the bone anchoring device.
Figures 2, 3:
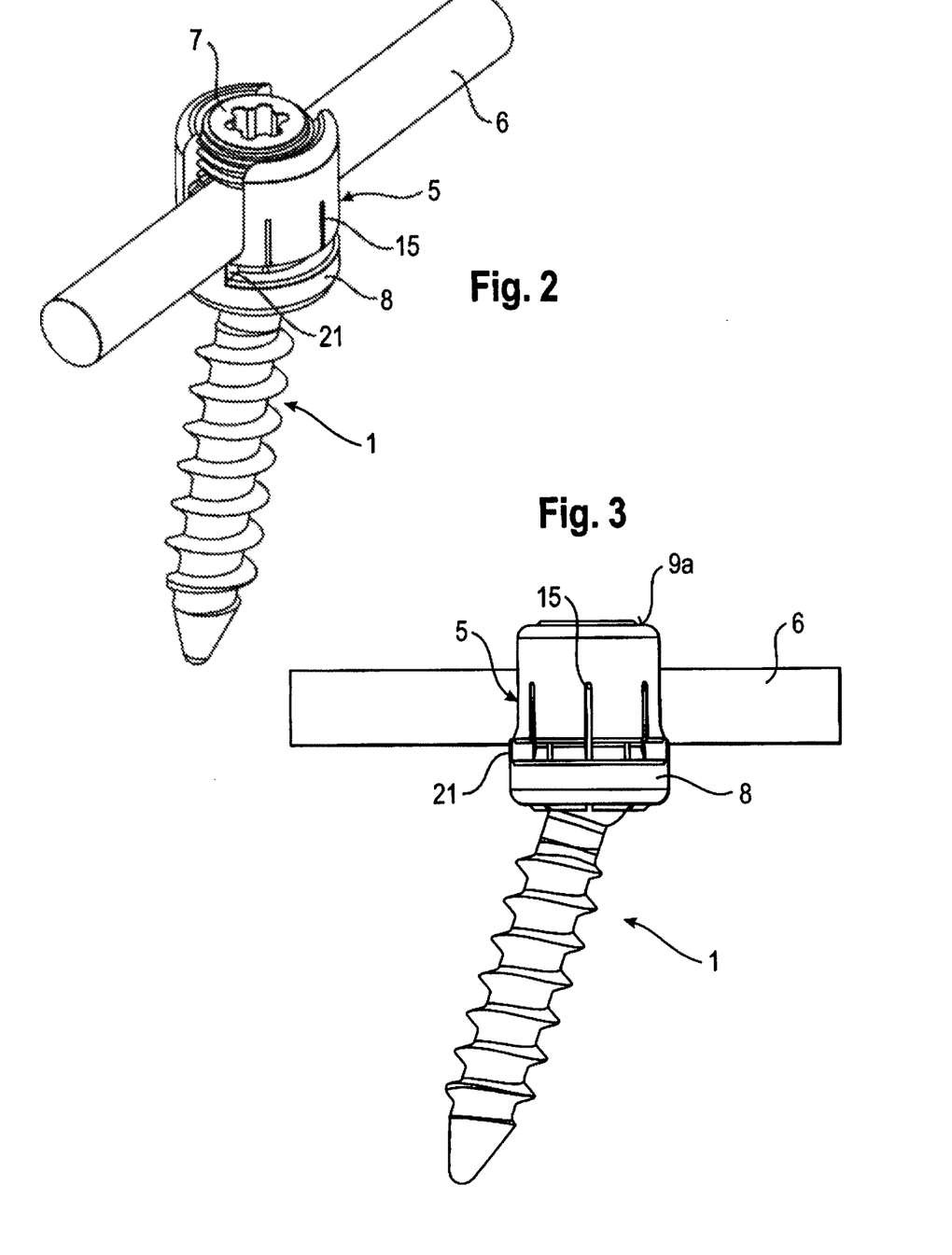
FIG. 2 shows a perspective view of the bone anchoring device of FIG. 1 in an assembled state.
FIG. 3 shows a side view of the bone anchoring device of FIG. 2.
Figure 5:
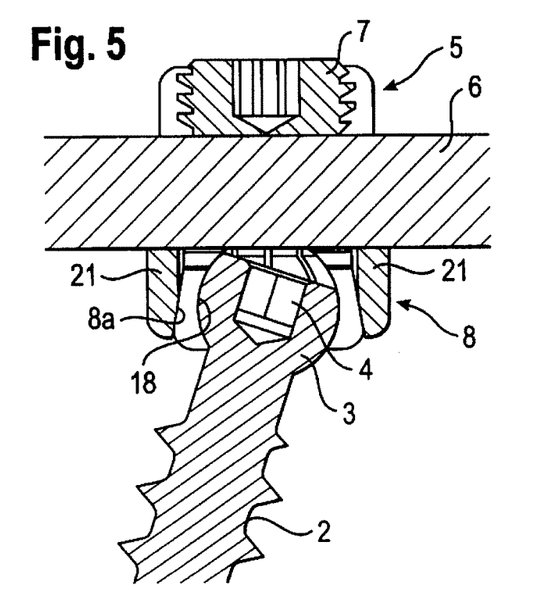
FIG. 5 shows a partial sectional view of the bone anchoring device according to FIGS. 1 to 3 the section being made in a plane containing the rod axis.
Figure 6:
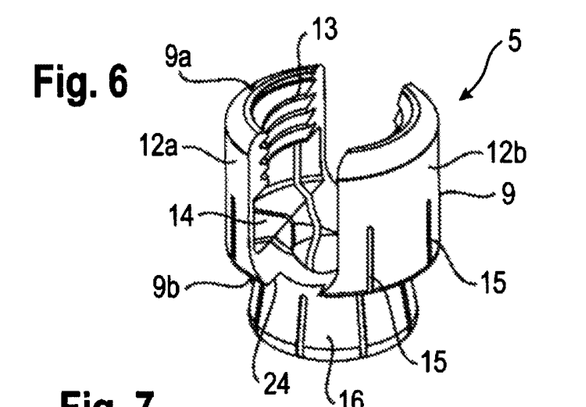
FIG. 6 shows a perspective view of the receiving part of the bone anchoring device according to the first embodiment.
Figure 7:
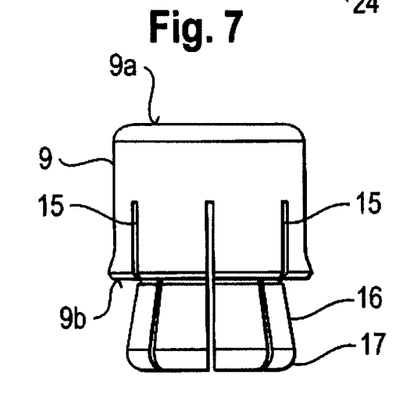
FIG. 7 shows a side view of the receiving part of FIG. 6.
Figure 8:
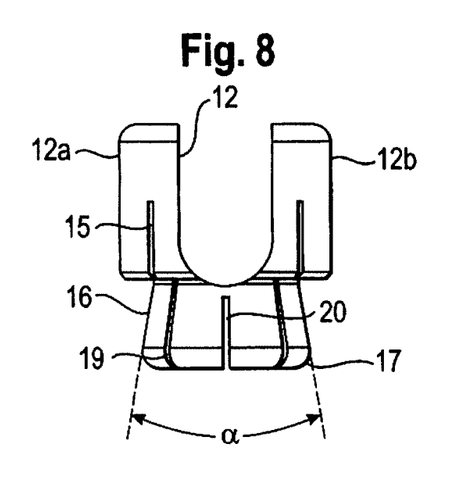
FIG. 8 shows a side view of the receiving part of FIG. 7 rotated by 90°.
Figure 9:
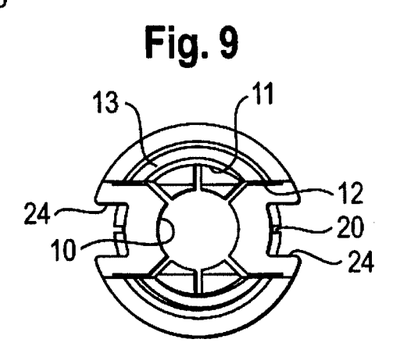
FIG. 9 shows a top view of the receiving part of FIG. 6.
Figure 10:
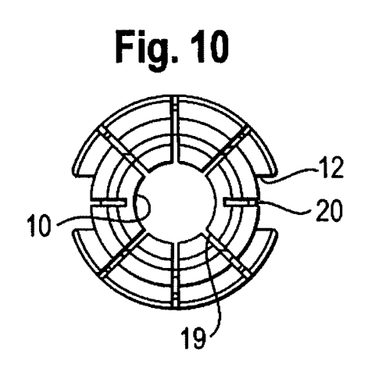
FIG. 10 shows a bottom view of the receiving part of FIG. 6.

As can be seen in particular in FIGS. 1, 2 and 5, the locking ring 8 further comprises on its side facing the second end 9b two projections 21 located diametrically opposite to each other. The projections 21 have such a height that they project above the bottom of the U-shaped recess 12 and extend into the cuts 24 when the locking ring is in a position in which the head 3 is not yet clamped. The free end 22 of the projections 21 can be curved with a curvature corresponding to that of the rod 6. The locking ring is arranged in such a way around the second portion 16 of the receiving part 5 that the projections 21 are located at the positions of the U-shaped recess 12. By means of this, the projections 21 which project into the U-shaped recess 12 prevent the locking ring from rotating when the rod is not inserted.

The inner screw 7 has a thread cooperating with the internal thread 13 provided on the legs. If a thread form which prevents the legs from splaying is used, a single closure element such as the inner screw 7 is sufficient. This reduces the size of the bone anchoring device in a radial direction.

The receiving part, the locking ring, the inner screw and the bone anchoring element are made of a biocompatible material, for example of titanium or stainless steel or a biocompatible plastic material with sufficient strength.

The bone anchoring device may be preassembled with the locking ring which is mounted on the second portion 16 of the receiving part 5 from the free end 17. Alternatively, the bone anchoring element 1 can be preassembled with the receiving part 5 and the locking ring 8.

The bone anchoring device can be used in several ways. In one way of use the bone anchoring element, the receiving part and the locking ring are preassembled. The bone anchoring element is screwed into the bone with the receiving part mounted to the anchoring element. The recess 4 of the head can be accessed with a screwing-in tool through the first bore 10. The locking ring 8 is in its first position close to the second end 9b where does not clamp the head 3. In this state, the head 3 is pivotably held in the second portion 16 which allows the receiving part 5 to be aligned to receive the rod. Once the correct position of the rod with respect to other bone anchoring devices is achieved, the inner screw 7 is screwed between the legs until it presses onto the rod. The rod is pressed against the bottom of the U-shaped recess thereby engaging the free ends 22 of the projections 21, respectively, and shifting down the locking ring 8.

When the locking ring 8 is moved toward the free end 17 of the second portion, it compresses the second portion 16 thereby clamping the head 3. Since the force which is exerted by the locking ring acts from the lateral side, the force necessary for safely immobilizing the head is smaller than in the case in which the force acts from above on the top of the head 3. This also allows to downsize the device by allowing the wall thickness of the receiving part to be reduced.

Final tightening of the inner screw locks the rod and the head simultaneously.

In another way of use, only the receiving part 5 and the locking ring 8 are preassembled.

The bone anchoring element 3 is first screwed into the bone and then the receiving part is clicked onto the head 3 while the locking ring 8 is in its first position close to the second end 9b and does not compress the second portion 16. Alternatively, the bone anchoring element 1 and the receiving part with preassembled locking ring are assembled by the surgeon by clicking the receiving part onto the head 3. This allows the surgeon to select the appropriate bone anchoring element in terms of diameter and length of the anchoring section.

In yet another way the head can be locked independently of the rod, if, as described above, the cooperating surfaces of the locking ring and the second portion are designed so as to allow a preliminary fixation.

Figure 11:
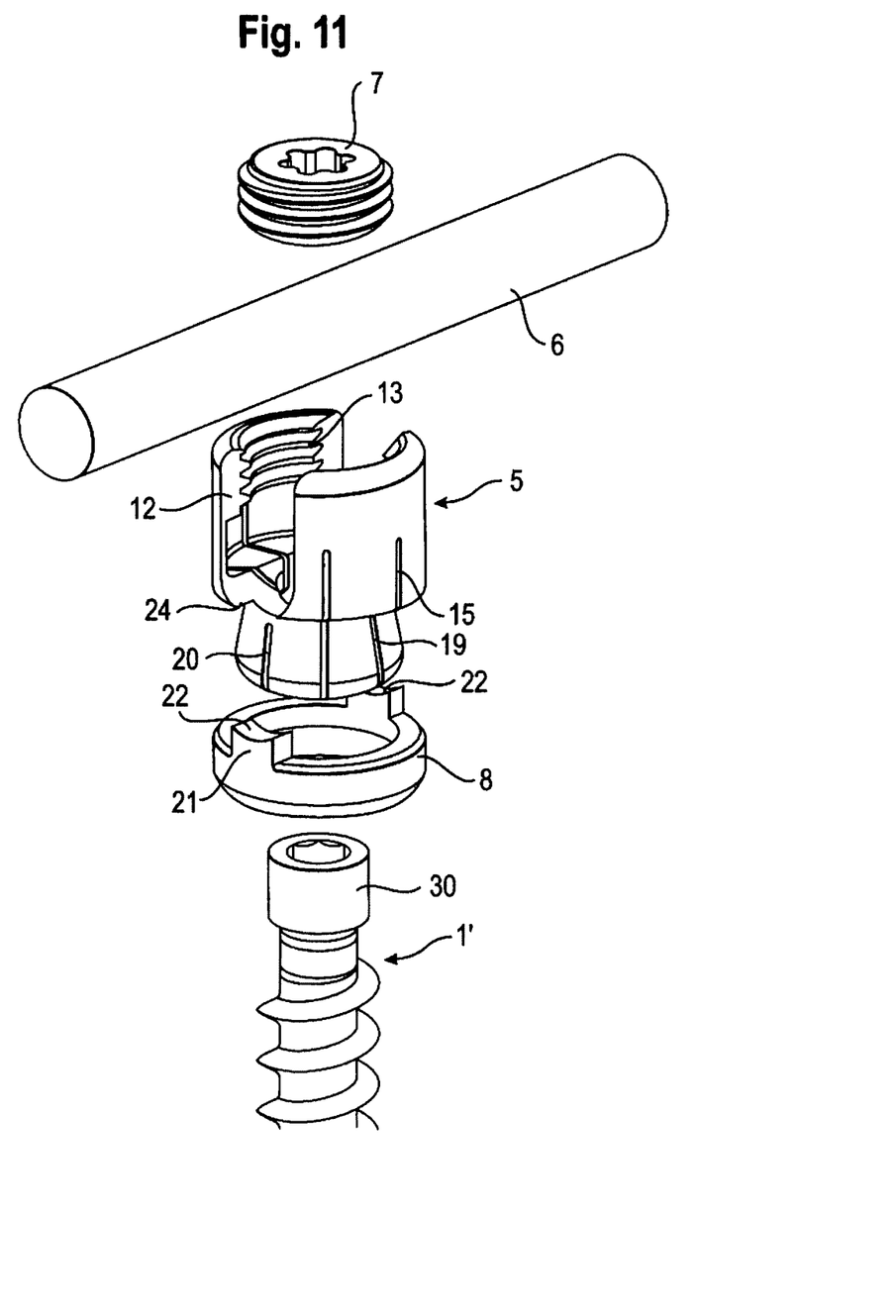
FIG. 11 shows a perspective exploded view of the bone anchoring device according to a second embodiment.
Figure 12:
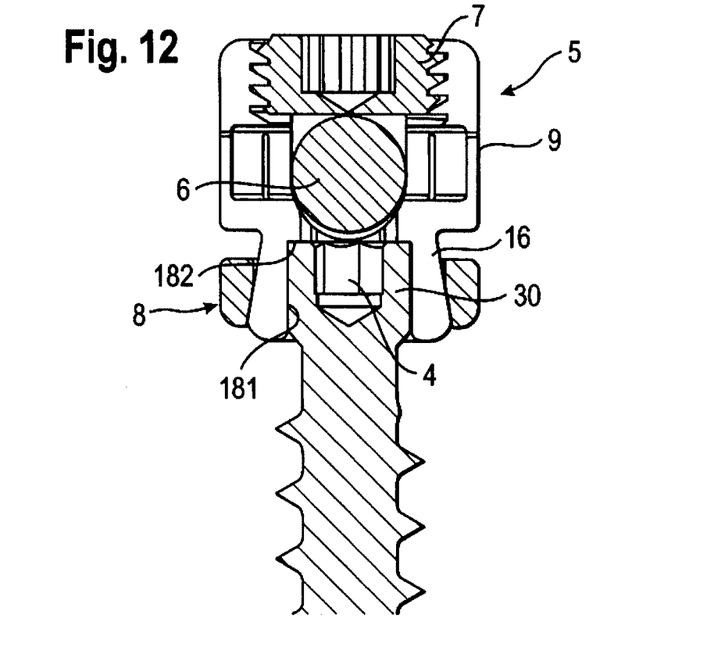
FIG. 12 shows a partial sectional view of the bone anchoring device of FIG. 11 in an assembled state, the section being perpendicular to the rod axis.
Figure 13:
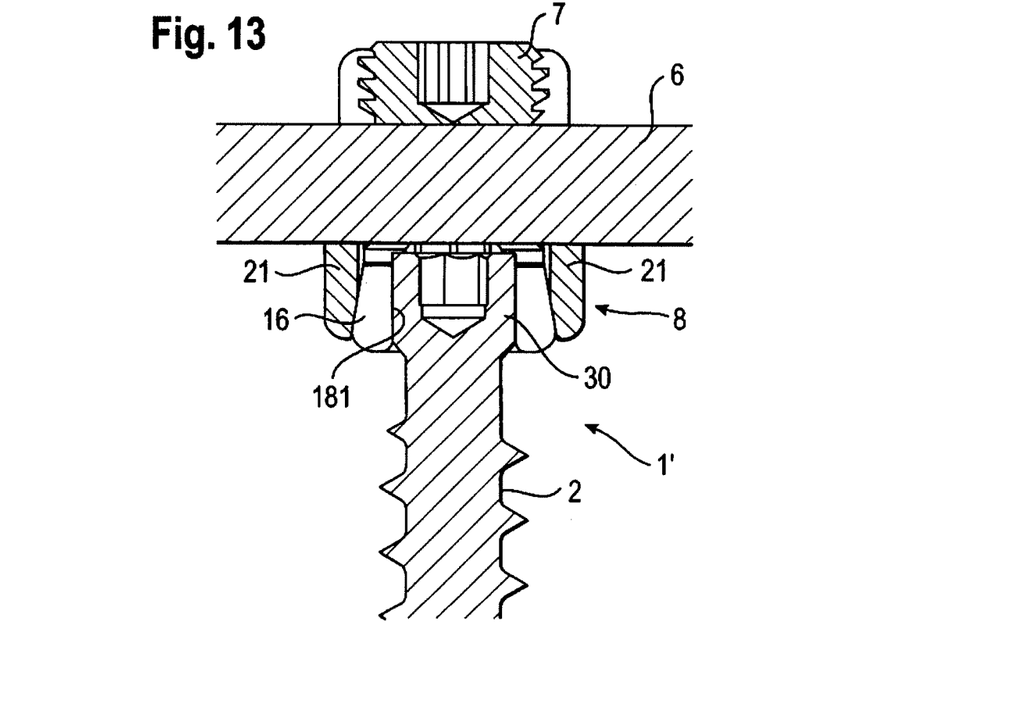
FIG. 13 shows a partial sectional view of the bone anchoring device of FIG. 12, the section being taken in a plane containing the rod axis.

FIGS. 11 to 13 show a second embodiment of the bone anchoring device. Portions and elements which are identical to the first embodiment are designated with the same reference numerals as in the description of the first embodiment. The description thereof will not be repeated.

The second embodiment differs from the first embodiment only with respect to the bone anchoring element and the accommodation space in the second portion 16 of the receiving part. The bone anchoring element 1' has a threaded shaft 2 and a cylindrical head 30. As can be seen in particular in FIGS. 12 and 13, the accommodation space of the second portion 16 of the receiving part 5 has a hollow cylindrical inner space 181 the diameter of which is slightly larger than the diameter of the cylindrical head 30 in such a way that the cylindrical head 30 can be inserted and guided in the cylindrical section 181 in the unlocked state. The end of the cylindrical section forms a stop 182 for the head 30. The use of the bone anchoring device according to the second embodiment is similar to that of the first embodiment. The difference is that the receiving part 5 cannot pivot relative to the bone anchoring element 1' but can only rotate in the unclamped state of the head 30. Such a monoaxial rotatable connection between the receiving part 5 and the bone anchoring element 1', allows the receiving part to be aligned with respect to the rod by only rotating it around the screw axis which may be useful in certain anatomical situations.

Figure 14:
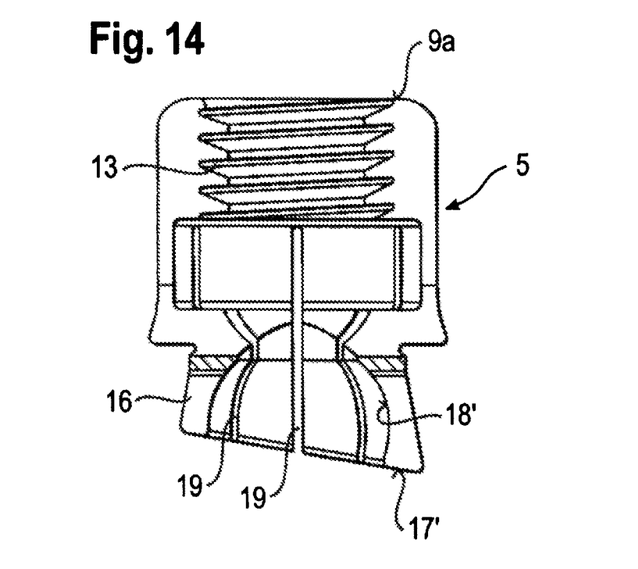
FIG. 14 shows a sectional view of the receiving part of a third embodiment of the bone anchoring device.
Figure 15:
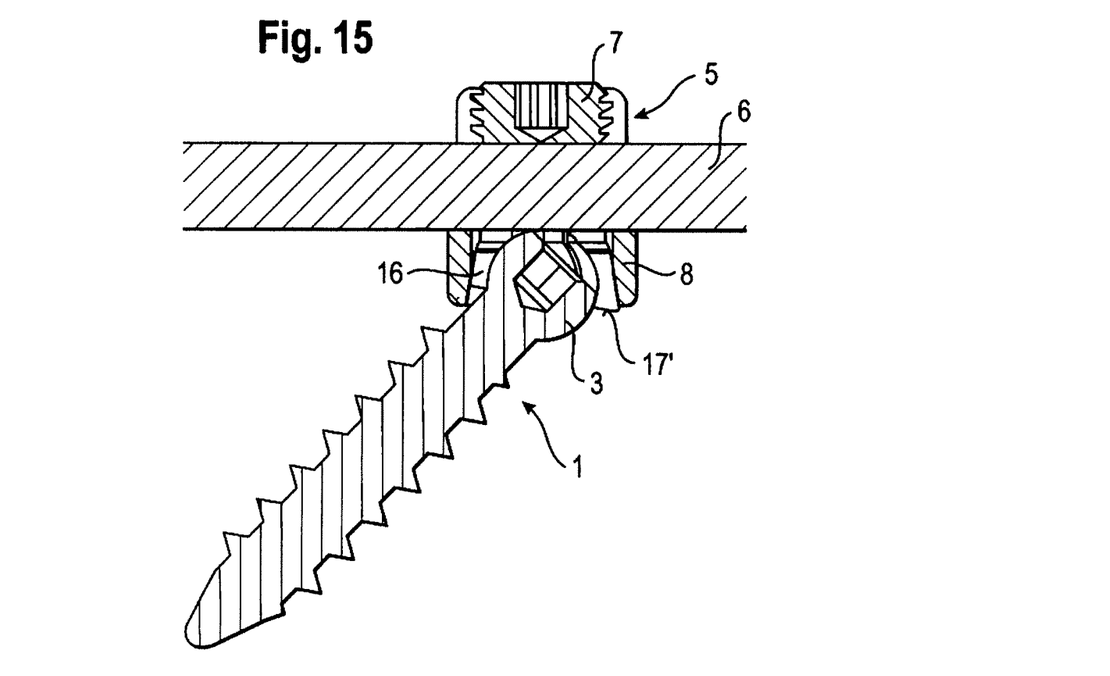
FIG. 15 shows a sectional view of the bone anchoring device according to the third embodiment.

FIGS. 14 and 15 show a third embodiment of the bone anchoring device. Portions and elements which are identical to the first embodiment are designated with the same reference numerals as in the description of the previous embodiments and the detailed description thereof will not be repeated. The receiving part 5 of the third embodiment comprises an inclined free edge 17' of the second portion 16. As can be seen in particular in FIG. 14, the inclined free end 17' defines a plane which includes an angle with the plane defined by the first end 9a of the first portion of the receiving part. The hollow spherical section 18' which accommodates the head 3 is therefore shorter on one side compared to the opposite side.

As can be seen in FIG. 15 this results in a larger pivot angle to one side as compared to the opposite side. Hence, a polyaxial screw with an asymmetric pivot angle range is provided. The inclined free end 17' can be easily manufactured by cutting.

Figure 16:
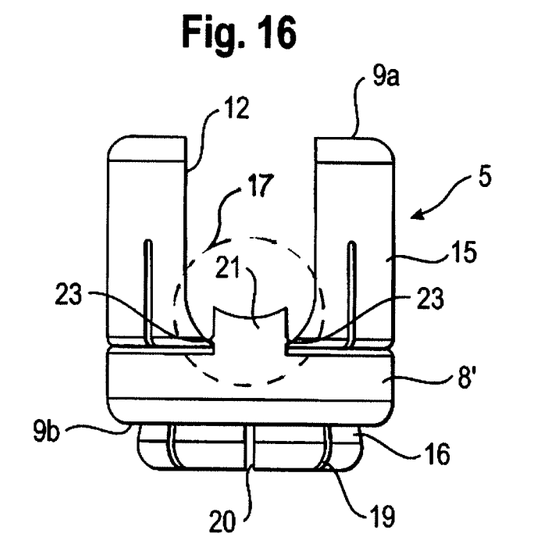
FIG. 16 shows a modification of the receiving part with the locking ring of the previous described embodiments.
Figure 17:
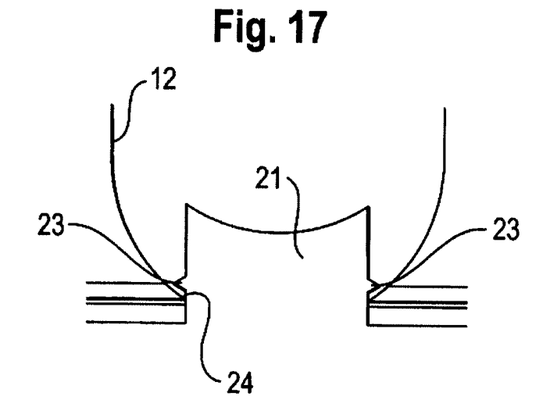
FIG. 17 shows an enlarged portion 17 of FIG. 16.

FIGS. 16 and 17 show a modification of the locking ring. The receiving part 5 is identical to one of the previously described receiving parts and the description thereof will not be repeated. The locking ring 8' has on either side of each projection 21 a lateral projection 23 resulting in a diameter of the projection 21 being larger than the diameter of the cuts 24. When the locking ring 8' is mounted, the projections 23 snap into the recess 12 due to the elasticity of the receiving part 5. The projections 23 form a securing means against falling off of the locking ring 8' when the head 3 is not yet inserted. This may be useful when the surgeon handles the parts before the receiving part 5 is clicked onto the screw.

Figure 18:
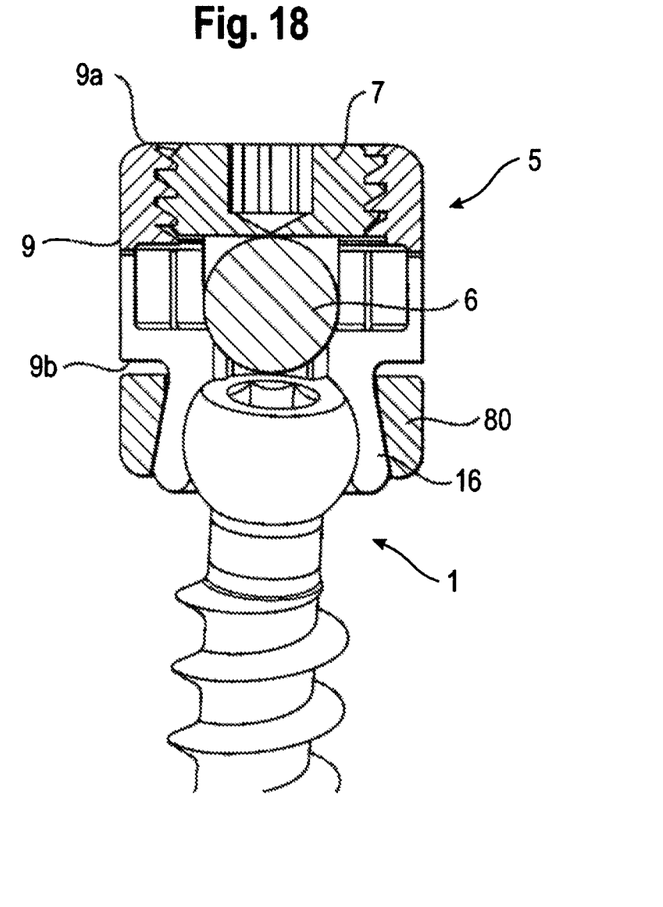
FIG. 18 shows a further modification of the bone anchoring device.

FIG. 18 shows a further embodiment which differs from the previous embodiments in that the locking ring 80 has no projections 21. As can be seen in FIG. 18, the height of the locking ring 80 is larger and the U-shaped recess 12 extends deeper into the receiving part such that the rod 6 can directly press onto the locking ring 80.

Figures 19, 20, 21:
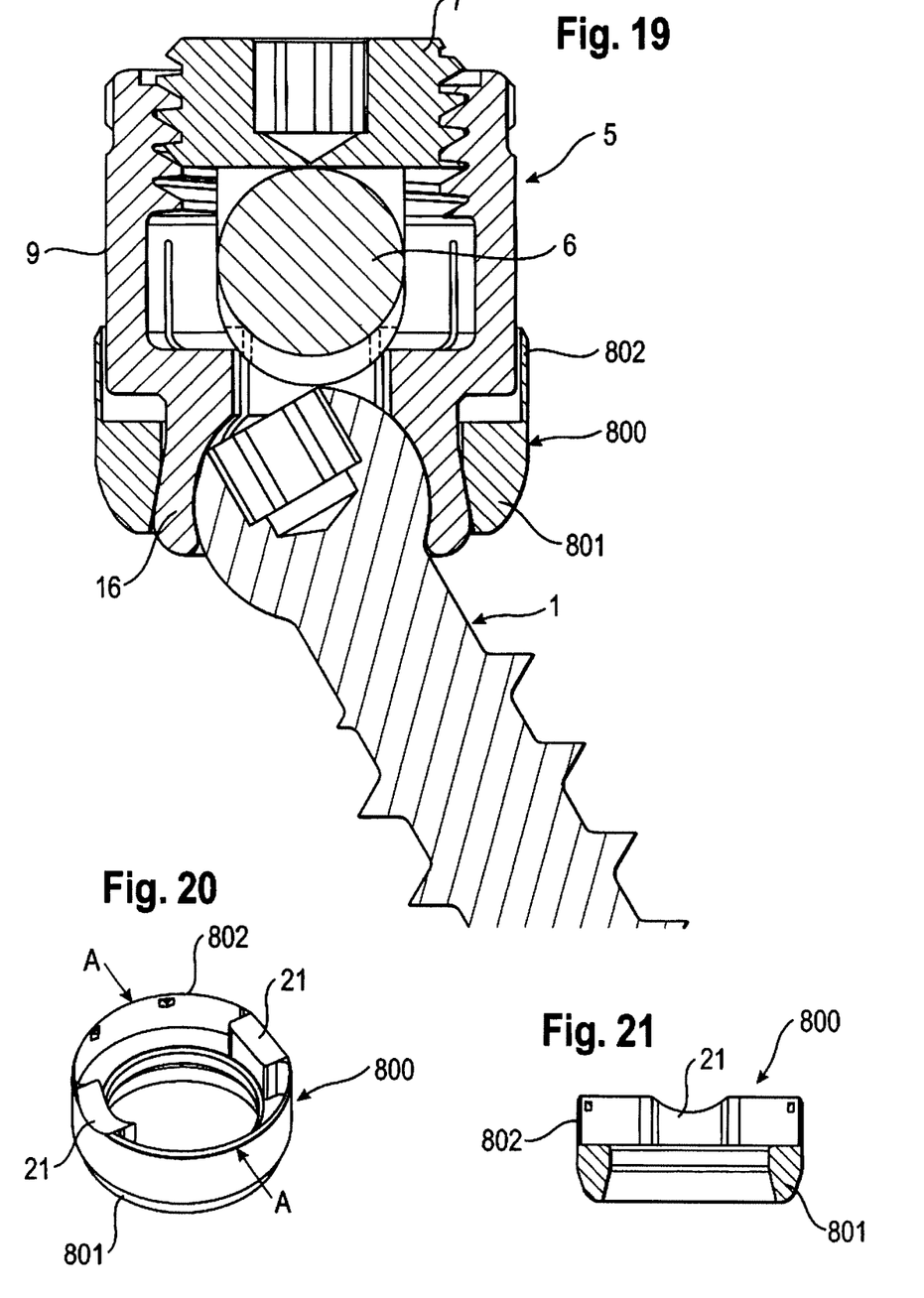
FIG. 19 shows a partial sectional view of a further embodiment.
FIG. 20 shows a perspective view from above onto the locking ring of the embodiment according to FIG. 19.
FIG. 21 shows a sectional view of the locking ring of FIG. 20 along line A-A.

FIG. 19 shows a further embodiment which differs from the embodiment according to FIG. 1 in the design of the locking ring 800. The receiving part 5 is identical to one of the previously described receiving parts and the description thereof will not be repeated. The locking ring 800 has a lower part 801 which is designed like the locking ring 8 of, for example, FIGS. 11 to 13 and includes two projections 21 which are offset by 180°. Furthermore, the locking ring 800 includes an annular edge 802 the inner diameter of which is larger than the outer diameter of the first portion 9 of the receiving part 5. The height of the annular edge 802 can be as large as the height of the projection 21. However, the annular edge 802 can have a height larger than the projection 21. The thickness of the annular edge 802 is small, so that the overall diameter of the receiving part 5 is not substantially increased.

As can be seen in FIG. 19, the annular edge 802 has such a height that when the locking ring 800 is in its lower most position clamping the head of the screw 1 the annular edge 802 closes the gap between the main portion 801 of the locking ring and the lower side of the first portion 9 of the receiving part. Therefore, there is not risk of in-growth of tissue or vessels into this place.

Further modifications of the embodiments described are possible. For example, the head of the bone anchoring element can have any other shape, such as, for example, a conical shape and the accommodation space in the second portion 16 of the receiving part is adapted to this shape. In a further modification the receiving part 5 or at least the second portion 16 are made of a biocompatible plastic material which provides elasticity to a certain degree. In this case, the slits may be omitted. The projections of the locking ring which engage the rod can have another shape. For example, the surface of the free end can be flat or otherwise shaped. Instead of selecting the cone angle to achieve self-locking between the locking ring and the second portion a preliminary locking of the head while the rod is still movable can be achieved by providing surface structures on the contacting surfaces such as ribs or a roughened surface.

What is claimed is:

1. A bone anchoring device comprising:
    a bone anchoring element having a shaft for anchoring to a bone and a head;
    a receiving part for coupling a rod to the bone anchoring element, wherein the receiving part comprises:
        a first portion comprising two legs each having a free end and defining a U-shaped recess for receiving the rod; and
        a second portion defining an accommodation space for accommodating the head, the second portion having a free end and being flexible to allow introduction of the head into the accommodation space and clamping of the head when the head is in the accommodation space; and
    a locking ring configured to be mounted to the receiving part from the free end of the second portion and to be positioned around the second portion, the locking ring comprising at least one projection configured to be positioned in the U-shaped recess and a structure on the projection configured to engage the receiving part for restricting axial movement of the locking ring relative to the receiving part; and
    wherein when the head is in the accommodation space, the locking ring is configured to compress the second portion of the receiving part to lock a position of the head relative to the receiving part.

2. The bone anchoring device according to claim 1, wherein the diameter of the second portion of the receiving part adjacent to the first portion of the receiving part is smaller than the diameter of the first portion adjacent to the second portion.

3. The bone anchoring device according to claim 1, wherein the locking ring is movable along the second portion of the receiving part between a first position limited by the first portion and a second position limited by the free end of the second portion.

4. The bone anchoring device according to claim 1, wherein the outer diameter of the locking ring is smaller than or equal to the outer diameter of the first portion.

5. The bone anchoring device according to claim 1, wherein the second portion of the receiving part has a conical outer surface tapering toward the first portion.

6. The bone anchoring device according to claim 5, wherein the locking ring has a section with a conically tapering inner surface corresponding to the conical outer surface of the second portion.

7. The bone anchoring device according to claim 6, wherein a cone angle is selected to provide self-locking between the locking ring and the second portion.

8. The bone anchoring device according to claim 7, wherein the cone angle is between approximately 2° and approximately 10°.

9. The bone anchoring device according to claim 1, wherein the second portion comprises a plurality of slits open to the free end of the second portion.

10. The bone anchoring device according to claim 9, wherein at least one of the plurality of slits extends continuously from the second portion into the first portion.

11. The bone anchoring device according to claim 1, wherein the first portion comprises a plurality of slits extending from a distance from the free end of the legs toward the second end.

12. The bone anchoring device according to claim 1, wherein the head is spherical segment-shaped and the second portion comprises an inner surface with a corresponding spherical portion to allow a pivotal movement of the head.

13. The bone anchoring device according to claim 1, wherein the head is cylindrically-shaped and the second portion comprises an inner surface with a corresponding cylindrical portion to restrict the movement of the head to a rotational movement about a single axis.

14. The bone anchoring device according to claim 1, wherein a closure element is provided for securing the rod in the recess.

15. The bone anchoring device according to claim 1, wherein a plane going through the free end of the second portion is arranged at an angle to an end defined by the free ends of the legs.

16. The bone anchoring device according to claim 1, wherein at least the second portion comprises an elastic plastic material with no slits.

17. The bone anchoring device according to claim 1, wherein the locking ring and the second portion of the receiving part comprise respective contacting surfaces configured to come into contact with one another, and wherein at least one of the contacting surfaces comprises a surface structure to hold a position of the locking ring relative to the receiving part.

18. The bone anchoring device according to claim 17, wherein the surface structure comprises at least one rib or a roughened surface.

19. The bone anchoring device according to claim 1, wherein the locking ring has an annular edge extending in a same direction as the projection, and wherein the edge is configured to surround a portion of the first portion of the receiving part when the head is clamped.

20. A method of attaching a bone anchoring device to a bone or vertebrae, the bone anchoring device comprising a bone anchoring element having a shaft for anchoring to a bone and a head, a receiving part for coupling a rod to the bone anchoring element, wherein the receiving part comprises a first portion comprising two legs each having a free end and defining a U-shaped recess for receiving the rod, and a second portion defining an accommodation space for accommodating the head, the second portion having a free end and being flexible to allow introduction of the head into the accommodation space and clamping of the head when the head is in the accommodation space, and a locking ring configured to be mounted to the receiving part from the free end of the second portion and to be positioned around the second portion, the locking ring comprising at least one projection configured to be positioned in the U-shaped recess and a structure on the projection configured to engage the receiving part for restricting axial movement of the locking ring relative to the receiving part, the method comprising:
- attaching the bone anchoring element to a bone or vertebrae;
- inserting the head of the bone anchoring element into the accommodation space of the the second portion of the receiving part;
- inserting the rod in the U-shaped recess; and
- exerting pressure on the locking ring by the rod to move the locking ring to a position where the locking ring compresses the second portion of the receiving part to lock a position of the head relative to the receiving part.

* * * * *